(12) United States Patent
Brady et al.

(10) Patent No.: US 8,168,840 B2
(45) Date of Patent: May 1, 2012

(54) BIOMASS PRETREATMENT PROCESS

(75) Inventors: Michael Brady, Studio City, CA (US); Paul O'Connor, Hoevelaken (NL); Dennis Stamires, Dana Point, CA (US)

(73) Assignee: KiOR Inc., Pasadena, TX (US)

( * ) Notice: Subject to any disclaimer, the term of this patent is extended or adjusted under 35 U.S.C. 154(b) by 0 days.

(21) Appl. No.: 12/921,343

(22) PCT Filed: Jun. 25, 2009

(86) PCT No.: PCT/EP2009/057955
§ 371 (c)(1),
(2), (4) Date: Jan. 26, 2011

(87) PCT Pub. No.: WO2009/156464
PCT Pub. Date: Dec. 30, 2009

(65) Prior Publication Data
US 2011/0114876 A1    May 19, 2011

Related U.S. Application Data

(60) Provisional application No. 61/075,563, filed on Jun. 25, 2008.

(51) Int. Cl.
*C10G 1/00* (2006.01)
(52) U.S. Cl. .............. 585/242; 585/240; 585/14; 127/2; 44/605
(58) Field of Classification Search ................... 585/14, 585/240, 242; 44/605; 127/2
See application file for complete search history.

(56) References Cited

U.S. PATENT DOCUMENTS

| | | | | |
|---|---|---|---|---|
| 4,118,271 A * | 10/1978 | Oku et al. | ........................ | 162/31 |
| 4,880,473 A | 11/1989 | Scott et al. | | |
| 5,338,366 A * | 8/1994 | Grace et al. | ....................... | 127/37 |
| 5,395,455 A | 3/1995 | Scott et al. | | |
| 5,597,714 A | 1/1997 | Farone et al. | | |
| 5,705,216 A | 1/1998 | Tyson | | |
| 5,807,952 A | 9/1998 | Agblevor | | |
| 6,692,578 B2 | 2/2004 | Schmidt et al. | | |
| 2005/0069998 A1 | 3/2005 | Ballesteros Perdices et al. | | |
| 2009/0090046 A1* | 4/2009 | O'Connor et al. | .............. | 44/307 |

FOREIGN PATENT DOCUMENTS

| | | |
|---|---|---|
| EP | 1852466 | 7/2007 |
| EP | 1852492 | 7/2007 |
| EP | 1889870 | 2/2008 |
| WO | WO00/74909 | 12/2000 |
| WO | WO2006/085762 | 8/2006 |
| WO | WO 2007/111605 | * 10/2007 |
| WO | WO2007/128799 | 11/2007 |
| WO | WO2008/009644 | 2/2008 |
| WO | WO2008/073186 | 6/2008 |
| WO | WO2009/156464 | 12/2009 |

OTHER PUBLICATIONS

Antal, M., In Adv. in Solar Energy vol. 2, Amer. Solar Energy Soc., NY, (1983).
Antal J., "Cellulose Pyrolysis Kinetics: the Current State of Knowledge" Ind. Eng. Chem. Res., 34: 703-717, (1995).
Bridgwater, A.V., "Catalysis in Thermal Biomass Conversion," Appl. Catalysis A, 116:5-47, (1994).
Cabradilla K.E. and Zeronian S.H., "Influence of Crystallinity on the Thermal Properties," Thermal Uses and Properties of Carbohydrates and Lignins, Academic Press (1976).
Chang V.S. , et al., "Fundamental Factors Affecting Biomass Enzymatic Reactivity," Appl. Biochemistry and Biotechnology, 84:5-37, (2000).
DeGroot, W et al "The Effects of Ion-Exchanged Cobalt Catalysts on the Gasification of Wood Chars in Carbon Dioxide," F. Fuel, 67:345-351,(1988).
Fahmi R. et al, "The Effect of Alkali Metals on Combustion and Pyrolysis of *Lolium* and *Festuca* Grasses, Switchgrass and Willow," Fuel. 86: 1560-1569, (2007).
Feldmann, et al. Amer. Chem. Soc., Symp. Ser. No. 144, ACS, Washington, DC, (1982).
Gray, R., et al. "Pyrolysis of a Wood-Derived Material. Effects of Moisture and Ash Content," Ind. Eng. Chem. Process Dev., 24(3): 646-65, (1985).
Hsisheng Teng and Yun-Chow Wei, "Thermogravimetric Studies on the Kinetics of Rice Hull Pyrolysis and the Influence of Water Treatment," Ind. Eng. Chem. Res. 37:3806-3811, (1998).
Hsu, T.A. et al., "Alcohol from Cellulose," Chemtech, 315-319, (1980).
Krässig H.A. et al, "Cellulose: Structure, Accessibility and Reactivity," Polymer Monographs vol. 11. 202, (1993).
Lappas, A., et al., "Biomass Pyrolysis in a Circulating Fluid Bed Reactor for the Production of Fuels and Chemicals," Fuel. 81: 2087-2095, (2002).
Liden, et al., "A Kinetic Model for the Production of Liquids from the Flash Pyrolysis of Biomass," Chem. Eng. Comm 65:207-221, (1988).
Mantanis G. et al., "Swelling of Wood. Part III. Effect of Temperature and Extractives on Rate and Maximum Swelling," Holzforschung, 49:239-248, (1995).

(Continued)

*Primary Examiner* — Nina Bhat
(74) *Attorney, Agent, or Firm* — Greenberg Traurig, LLP

(57) ABSTRACT

A process is described for pretreating lignocellulosic biomass. The process comprises swelling the lignocellulosic biomass with an aqueous liquid. The pretreated lignocellulosic biomass may be used as a feedstock for the enzymatic conversion to ethanol, or in a thermal conversion. process to produce bio-oil. The pretreatment results in a greater yield and, in the case of a thermal conversion process, a better quality of the bio-oil. The pretreatment process may be used to adjust the composition and amount of inorganic material present in the lignocellulosic biomass material.

20 Claims, No Drawings

OTHER PUBLICATIONS

Mantanis G., et al., "Swelling of Wood," Wood Sci. Technol. 28: 119-134, (1994).

Mohan D. et al., "Pyrolysis of Wood/Biomass for Bio-oil: A Critical Review" Energy and Fuels, 2006, 20 (3), pp. 848-889.

Mosier N. et al, "Features of Promising Technologies for Pretreatment of Lignocellulosic Biomass," Bioresource Technology. 96: 673-686, (2005).

Pan W-P et al. "Influence of Metal Ions on Volatile Products," Analytical & Applied Pyrolysis. 16: 117-126, (1989).

Penn, W.S. "Vuclanised Fibre"; The Electrical Manufacturer; 5(1): 8-10, (1949).

Raveendran et al, "Influence of Mineral Matter on Biomass Pyrolysis Characteristics," Fuel. 74(12):1812-1822, (1995).

Samolada, M.C., et al, "Catalyst Evaluation for Catalytic Biomass Pyrolysis," Energy and Fuels. 14:1161-1167, (2000).

Samolada, M.C., and Vasalos, I.A., "A Kinetic Approach to the Flash Pyrolysis of Biomass in a Fluidized Bed Reactor," Fuel 70:883-890, (1991).

Shafizadeh F. "Thermal degradation of cellulose", Cellulose Chemistry and Its Application, Chapter 11. T.P. Nevell and S.H. Zeronian (Eds),Ellis Horwood Ltd. 266, (1985).

Shafizadeh F. et al. "Combustion Characteristics of Cellulosic Fuels" Thermal Uses and Properties of Carbohydrates and Lignins. In Shafizadeh F, Sarkanen KV, Tillman DA, eds. New York: Academic Press, 1-17, (1976).

Shafizadeh, J. "The Influence of Exchangeable Cations on the Carbonization of Biomass," Pyrolysis, 6:217-232,(1984).

Soderstrom J. et al., "Two-Step Steam Pretreatment of Softwood by Dilute $H_2SO_4$ Impregnation for Ethanol Production," Biomass and Bioenergy. 24:475-486, (2003).

Stamm A., "Shrinking and Swelling of Wood," Ind. Eng. Chem. 27(4): 401-406, (1935).

Varhegyi, G., et al., "Simultaneous Thermogravimetric-Mass Spectrometric Studies of the Thermal Decomposition of Biopolymers. 1. Avicel Cellulose in the Presence and Absence of Catalysts," Energy & Fuels. 8:267-272, (1988).

Wangaard, et al., "The Effect of Extractives on Water-Vapor Sorption by Wood," Wood Sci. Technol. 1(4):253-277, (1967).

Wu M.M. et al, "Optimization of Steam Explosion to Enhance Hemicellulose Recovery and Enzymatic Hydrolysis of Cellulose in Softwoods," Appl. Biochemistry and Biotechnology, 77: 47-54, (1999).

Wyman C.E. et al, "Coordinated Development of Leading Biomass Pretreatment Technologies," Bioresource Technology, 96:1959-1966, (2005).

Zaror, C.A. et al., "Secondary Char Formation in the Catalytic Pyrolysis of Biomass," Fuel, 64:990-994, (1985).

International Search Report in International Application PCT/EP2009/057955 mailed Aug. 25, 2010.

* cited by examiner

BIOMASS PRETREATMENT PROCESS

BACKGROUND OF THE INVENTION

1. Field of the Invention

The invention relates generally to a process for pretreating biomass material prior to conversion to liquid fuel, and more particularly to a pretreatment process comprising soaking biomass material in an aqueous solvent, which may sometimes also contain additive(s). In a preferred embodiment the pretreatment process comprises removal of inorganic materials from the biomass material.

2. Description of the Related Art

World energy demand is projected to increase substantially due to: an increase in the world's population; improvement of the standard of living in underdeveloped countries; and depletion of the reserves of fossil fuels.

Now, generally recognized by major countries, global climatic changes caused by increasing emissions of greenhouse gases, such as $CO_2$, require that newly developed energy sources must be environmentally compatible and sustainable. Therefore, greener sources of energy are needed to replace or reduce the consumption of fossil fuels. Biomass is a sustainable and renewable source of fuel, with potentially a net zero greenhouse gas impact.

Biomass conversion technologies include: biological processes, such as anaerobic or aerobic fermentation; and thermal conversion processes, such as direct combustion for heating and generating electricity; gasification for producing syngas; and pyrolysis for producing biooils, which can be converted to fuels and chemicals.

The thermal conversion processes include hydrothermal processes, wherein biomass is treated in slurry form in autoclaves at temperatures above 200° C. and under autogenous pressures.

Pyrolysis processes have a high potential for large scale commercialization, as they provide flexibility in varying process conditions, such as heating rate, temperature, pressure, contact time, atmosphere, etc., to optimize yields of liquids (oil), gas and char. Of particular interest is fast (or flash) pyrolysis designed to convert the biomass to maximum amounts of oil, employing a very low residence time, a very high heating rate and temperatures up to 500° C. The oil produced has a high energy density that can be directly used in combustion or refined to fuels and specialty chemicals.

However, the pyrolysis-derived bio-oils, because of their high oxygen contents, high viscosity, corrosiveness and low stability, have limited direct applications as fuels. Intensive research is being now carried out to upgrade the quality of said bio-oils to products that are comparable to conventional fuels in composition, and chemical and physical properties.

Pretreatment processes of biomass before pyrolysis offer possible solutions in the form of biomass modification that will allow the pyrolysis process to be conducted at less severe conditions (i.e., lower temperatures, shorter contact times), and more efficiently in that more oil is produced, and the oil produces is of a better quality.

In an alternative approach, biomass conversion in large commercial plants is now carried out to produce ethanol, primarily using as feeds from renewable sources such as corn, sugar cane, and cereal grains. Because the cost of these raw materials represents roughly one-half of the total cost of the process to produce the ethanol, it is of paramount interest to use cheaper biomass raw materials for conversion to ethanol. Furthermore, it is important to utilize biomass sources other than grains, in order to minimize the impact on food prices.

Consequently, less costly lignocellulosic biomass materials derived from agricultural and forestry residues are very attractive for use as biomass sources to be converted to ethanol or other fuels.

The use of ethanol in automobile fuels not only reduces the need for petroleum (crude oil), but also substantially reduces the carbon dioxide car-exhaust emissions.

Commercial large scale operations involving the production of ethanol from cellulosic biomass use biological or non-biological processes to depolymerize (break down) the cellulose. The most commonly used biological processes use enzymes, whereas the nonbiological processes use an acid hydrolysis to convert the cellulose to sugars, mostly using dilute or concentrated sulphuric acid. These processes are considered as a pretreatment of the biomass in the overall bioconversion processes, which are followed by fermentation and distillation.

In the prior art one finds descriptions of other kinds of pretreatments such as steam explosion, which is followed by enzymatic hydrolysis, fermentation and distillation in the production of ethanol (see, C. E. Wyman et al, Bioresource Technology 96 (2005), 1959-1966).

Since the presently known processes for conversion of the lignocellulosic biomass (derived from agricultural and forestry residues) are more expensive than the processes used now commercially to produce ethanol from grains and cereals, there is strong interest in developing new or improved processes that will allow a more cost-effective and environmentally acceptable manner of converting lignocellulosic biomass (from residues derived from agriculture and forestry materials) to ethanol (see, N. Mosier et al, Bioresource Technology 96 (2005), 673-686).

In general, lignocellulosic biomass from such residues consists mainly of three components: cellulose, hemicellulose and lignin. The cellulose component is a polymer of glucose, formed in long strands. It is associated with the hemicellulose component layer, and both the crystalline cellulose and hemicellulose are encapsulated by the lignin cell wall.

In ethanol production from cellulosic biomass, the cellulose and hemicellulose are converted to sugars, such as glucose and xylose, followed by fermentation. Lignin is a 3-dimensional branched polyaromatic matrix acting as a sheath, or a protective coating to the cellulose and hemicellulose components of the biomass.

As a result, due to the differences in the bonding of the components, the high crystallinity of the cellulose, and the presence of the protective sheath of the lignin, the penetration of, and interaction with, the acids and/or the enzymes is highly impeded. This problem is much less observed when processing cereal grains to ethanol by converting the cellulose and hemicellulose to glucose, using acid or enzymatic hydrolysis.

However, for biomass from sources other than cereal grain, the lignin present resists the enzyme attack and hence lower yields are obtained. To at least partly overcome this problem, pretreatment of the biomass is necessary prior to subjecting the biomass to enzymatic hydrolysis. (see, T. A. Hsu, et al. Chemtech, May (1980), 315-319)

Since the major cost of the overall conversion process is due to the biomass feed and enzymes, it is necessary to minimize the use of enzymes and obtain the maximum conversion of the carbohydrates to ethanol.

For these reasons, a considerable amount of R&D work has been devoted during the last few years for developing means to pretreat the lignocellulosic biomass in such ways that the accessible surface area increases, which will allow an increase in the biomass ethanol conversion. The most popular processes are acid and enzymatic hydrolysis processes, which are used mostly to convert the cellulose and hemicellulose to glucose.

In the prior art there are several versions of the original acid hydrolysis process. These involve very concentrated acids or dilute acids, in one or two step treatments, and combinations of acid treatment with steam treatments, such as steam-explosion.

Overall, the pretreatment processes utilizing acids such as sulphuric acid, require specially constructed plant equipment that must be resistant to acid corrosion. Additionally, the use of acid requires neutralization by a low-cost base such as calcium hydroxide, and the formed sulphate salt must be filtered and washed from the biomass. This creates large waste streams that require disposal and lead to additional costs. Further, for the use of highly concentrated acids, the process requires an additional evaporator to produce/recycle the highly concentrated acid.

The acid pretreatments of lignocellulosic biomass feeds used to convert the cellulose and hemicellulose to fermentable sugars have certain disadvantages relating to higher costs, lower efficiencies and environmental problems. Specifically, processes using a high acid concentration have disadvantages relating to corrosion of equipment, and high cost waste stream disposal, whereas the dilute (low acid concentration) process produces a low conversion of the biomass to fermentable sugars.

Pretreatments using steaming (steam-explosion) as such and combinations with acid treatments have certain disadvantages. During steam-explosion pretreatments, the pentoses and hexoses produced from the hydrolysis of the cellulose material are to some extent further converted to undesirable by-products, such as furfural, levulinic acid (4-oxopentanoic acid) and formic acid, together with other products. (see, M. M. Wu et al, Appl. Biochemistry and Biotechnology 77 (1999) 47-54)

In general, processes involving acid treatments and steam-explosion produce compounds such as aliphatic acids, phenolic and furan derivatives. These degradation products act as inhibitors in subsequent processes using enzymes to convert the sugars to ethanol. (see, V. S. Chang, et al., Appl. Biochemistry and Biotechnology 84 (2000) 5-37)

Further, although high severity steam explosion allows the enzymes to react more effectively, it does degrade the produced sugars and reduces the yields, as well as making the lignin less reactive. Using less severe steaming-acid pretreatments produces lower glucose yields, since the enzymes cannot react with a major part of the cellulosic material. (see, J. Soderstrom, et al., Biomass and Bioenergy 24 (2003), 475-486—U.S. Pat. No. 4,880,473 and U.S. Pat. No. 6,692,578, U.S. Patent Applic. #US2005/0069998A1, U.S. Pat. No. 5,597,714, WO20061085762 A1)

Enzymatic hydrolysis presents a promising process for large-scale operations using lignocellulosic biomass, as it is low-energy intensive, environmentally compatible and does not require the use of corrosive chemicals. The main disadvantage of this process has been the cost of producing the enzymes, even though during the most recent years, with new improved processes, such cost has been reduced. (see, V. S. Chang et al., Applied Biochemistry and Biotechnology 84 (2000) 5-37)

Thus, there is need for developing pretreatment processes that allow the maximum conversion of lignocellulosic biomass to ethanol via high yield enzymatic hydrolysis, without the use of corrosive chemicals, waste streams and specialty high-cost equipment. There is a further need for such pretreatment processes that allow conversion of lignocellulosic biomass via pyrolysis process resulting in higher yields of bio-oil, as well as improved quality of bio-oil.

In general, any pretreatment of the lignocellulosic biomass to enhance its conversion must at least increase the micro- and macro-accessibility to the bulk of the particle allowing penetration of the enzymes and chemicals.

In the prior art, the term cellulases is used to describe a class of enzymes responsible for the biodegradation natural process. Cellulases are mainly produced by bacteria and fungi. For the purpose of this discussion, it is noted that the proteinic conveyors of the complex enzyme groups have molecular weights in the region of 30,000 to 100,000, and have globular shapes with hydrodynamic diameters in the range of 3 to 4 nm. Therefore, the openings of the cannulae, pores, cavities and interfibrillar interstices, must be large enough to allow molecules, ions, compounds, and enzymes to penetrate in the bulk of biomass. For an efficient enzymatic digestion and conversion, the biomass particle should have the largest possible number of such openings with diameters at least 3 to 4 nm. (see, H. A. Kzassig et al, in Polymer Monographs, "Cellulose", vol. 11 (1993) p 202.)

BRIEF SUMMARY OF THE INVENTION

The present invention addresses these problems by providing a process for pretreating a lignocellulosic biomass material, said process comprising the step of contacting the lignocellulosic biomass material with an aqueous fluid, causing the lignocellulosic biomass material to swell.

Another aspect of the invention comprises a method for adjusting the amount and composition of inorganic materials present in the lignocellulosic biomass material.

DESCRIPTION OF ILLUSTRATIVE EMBODIMENTS

The following is a description of certain embodiments of the invention, given by way of example only.

This invention is based on optimizing and utilizing the basic property of lignocellulosic materials, such as wood, which is the swelling and that is caused by polar liquids, such as water. Although this property of woods is a disadvantage for applications in construction, boards or packaging, etc., to the contrary, the swelling property of woods and other lignocellulosic materials is very useful for a pretreatment to a subsequent thermal conversion to bio-oil, or a subsequent enzymatic conversion of such lignocellulosic materials to ethanol. (see, Mentanis G., et al., Wood Sci. Technol. (1994), 28, 119-134. F. F. Wangaard, et al., Wood Sci. Technol. (1967) 1, 253-277).

This invention involves optimizing the water swelling process to affect penetration into the intercrystalline regions, reached through pores and capillaries leading into the interfibrillar spaces.

In particular, the objective of this invention is to provide materials and process conditions that cause optimum swelling, thereby that increases the accessibility and reactivity. Such optimum swelling involves both intrafibrillar and intercrystalline water penetration.

To increase the penetration of water to achieve maximum bulking or swelling, solutions of salts, acids, bases and organic water soluble compounds can be used, and preferably salts or inorganic bases. The paths that the water and solute molecules follow on their way into the bulk of the biomass involve the existing structural pores, capillaries and voids between fibrillar elements. As water molecules penetrate into interior of biomass particles, they cause disruption of fibrillar associations and move into regions interlinking the crystallite ensembles forming the fibrils. (see, A. Stamm, Ind. Eng. Chem. Vol. 27, No. 4 (1935) 401-406.)

Deeper penetrations, which require more severe process conditions and higher solute concentrations, involve the penetration of water solute molecules into the lattice structure of the crystallites, causing rupture of the hydrogen bonded layers and creation of accessible and reactive internal surfaces. The strong interaction of water and, for example, a strong inorganic base with the biomass, results in the opening of the intraplanar and interplanar hydrogen bonded links that cause lattice transformation, which in turn allows solute molecules and dissolved ions to diffuse between lattice layers. Usually, the swelling or bulking of the lignocellulosic materials by liquids causes corresponding changes in the dimensions of the wood particles. However, the changes, if any, in the dimensions of the particles do not necessarily reflect the amount of solvent absorbed in the bulk of the particle. This is due to the presence of fine and coarse capillaries within the bulk structure, which allow solvents (i.e., water) to fill the available space without causing measurable changes in the dimensions of the lignocellulosic mass.

The effectiveness of the solvent to cause swelling depends primarily on its basicity, hydrogen bonding affinity, and molecular bonding. The swelling properties of lignocellulosic materials (wood), as well as the ability of different chemicals to cause swelling have been studied for over 70 years. (see, A. Stamm, Ind. Eng. Chem. vol. 27, No. 4, 1934). Briefly, it has been show that the extent of swelling and solvent sorption can be related to the hydrogen bonding affinity of the solvent.

A simple model of the mechanism of the swelling process of wood with water involves the penetration of water molecules via capillaries into the bulk structure, whereby the water molecules first interact with the hydrogen-bonded hydroxyl groups of the lignocellulosic mass to form an energetically unstable transition-state. The hydroxyl group forms a water molecule, which is hydrogen-bonded to the lignocellulosic mass. Thus, this mechanism is based on a chemically activated process, and obeys the classical Arrhenius equation for chemical reactions requiring an activation energy.

Accordingly, the rate and extent of swelling substantially increase with increasing temperature. In one embodiment of the invention a lignocellulosic biomass is contacted with an aqueous fluid at an elevated temperature in the range of from 35° C. and 100° C. In another embodiment of the invention a lignocellulosic biomass is contacted with an aqueous fluid at an elevated temperature greater than 100° C. and, preferably, at autogenous pressure, as further described below. The interaction of water with the biomass can further be increased by the presence in the water of certain soluble salts. (see, A. Stamm, Ind. Eng. Chem. vol. 27, No. 4, 1934).

The "activity" of certain salts to increase swelling is in the following order:
Cations: $K<NH_4<Na<Ba<Mn<Mg<Ca<Li<Zn$ and
Anions: $ClO_3<SO_4<NO_3<Cl<Br<ClO_4<I<CNS$ However, there are exceptions to this order, depending on concentrations, temperature and kind of biomass used. In general, much more swelling occurs in alkaline solutions than in acidic solutions (see, Penn, W. S. (1949) Elec. Manuf. 5, (1), 8).

Certain salts (like concentrated $ZnCl_2$) used in hot solutions to cause swelling, react much further by splitting fibrillar aggregates and even dissolving parts of biomass. (see, Penn, W. S. (1949) Elec. Manuf. 5, (1), 8)

Bases, both organic and inorganic, have much more of an affinity to interact with biomass materials. According to one theory, cellulosic materials can be considered to exhibit chemical properties similar to mono-basic acids, which can be neutralized by contacting the biomass with strong bases.

In general, the affinity of certain bases to cause swelling for cellulosic materials can classified in the following order: $LiOH>NaOH>KOH>RbOH>CsOH$ (see, K. E. Cabradilla and S. H. Zeronian, "Influence of Crystallinity on the Thermal Properties" in Thermal Uses and Properties of Carbohydrates and Lignins, Academic Press (1976))

Briefly, and for the purpose of this invention, the action of water or other polar solvents and when enhanced by soluble salts bases or acids, but preferably with strong bases, and conducted at optimum temperature, concentration and pH result, to different extents, in the following:
(i) Rupture hydrogen bonds that hold together fibril aggregates creating more reactive bulk surface areas; and
(ii) Breaking of intraplanar and interplanar hydrogen bonds, allowing different biomass components to move, dissolve or rearrange as well as allow the soluble (salt) ions to penetrate to the interior of the biomass.

In one embodiment of the invention, the biomass material is pretreated for conversion to a bio-oil, the pre-treatment process comprising the steps of (i) swelling the biomass material with a solvent, optionally aided by pH control, application of mechanical action, the incorporation of additive(s) and temperature control; and (ii) removing solvent from the swollen biomass material by applying mechanical action to the biomass material. Preferably the solvent will be an aqueous liquid and the mechanical action will result in a particle size reduction of the biomass material. The mechanical action may be exerted by equipment selected from the group consisting of high shear mixers, kneaders, colloid mills, planetary mixers, mix-mullers, extruders, pressure filters, centrifuges and/or ball mills or other comminuting equipment. In one embodiment the solvent comprises an inorganic acid or inorganic base. Also, preferably the ash content of the biomass material will be reduced to less than 5 wt %, based on the dry weight of the biomass material and, more preferably, less than 3 wt %, based on the dry weight of the biomass material.

Overall, the bulk is now transformed to a sponge-like structure. The swelling widens the pores and capillaries creates exits to the surface, as well as opening of interfibrillar spaces now becoming available for reactions with chemical compounds, salt, acids, bases, as well as enzymes.

Biomass swollen with polar liquids like water, when it is dried (at 80-100° C.), does not allow all liquids present in the swollen regions to escape. This entrapment of the swelling agents and/or present solutes, like salts, is accompanied by some shrinkage of the biomass particles. Consequently, the swelling process followed by a drying step to entrap (encapsulate) chemical compounds, which may form inclusion complexes within the pores, voids, capillaries, interfibrillar interstices, provides a means for activating the biomass in a way that it becomes more reactive in a subsequent enzymatic conversion, or in a thermal or hydrothermal conversion for the production of fuels.

In general, lignocellulosic biomass, depending on its origin, contains, besides cellulose, hemicellulose and lignin, other components such as resins, tannins, terpenes, fats, etc. These materials, referred to as "extractables," can be removed by organic solvents, including alcohols. Additionally, the lignocellulosic biomass, depending on its kind and origin, contain a variety of metals. Mild treatments, like hot water (50-90° C.) can remove most of these "extractables" without altering the cellulosic components of the biomass. In general, the removal of "extractables" results in increasing the rate of diffusion of the solvent and solutes into the biomass, hence is increasing the size of the capillaries, disrupting the cell wall structure, and decreasing the network of secondary hydrogen bonds. Thus, the internal structure of the cell wall loses stability, which increases the reactivity of the exposed surfaces towards the solvent/solute molecules. Therefore, removal of the "extractables" increases the rate, as well as the extent of swelling. (see, G. Mantanis et al., Holzforschung, 49 (1995) 239-248; WO 00/74909 A1)

Lignocellulosic biomass, besides the organic extractable components, contains also inorganic extractables. About 20 kinds of metals have been identified in various kinds of lignocellulosic biomass, which vary not only with the kind of biomass, but also with its origin. In one embodiment of the current invention, the Fe content of the biomass material is reduced to less than 2,000 mg/kg, based on dry weight of the biomass material. In a more preferred embodiment, the Fe content of the biomass material is reduced to less than 1,000 mg/kg, based on dry weight of the biomass material.

The Role of Inorganic Matter Present in Biomass During Thermal Decomposition

Biomass conversion to fuels using thermal decomposition processes, such as combustion, carbonization, gasification, liquefaction, and pyrolysis, have received considerable attention during the last 30 years and, in particular, during the last 15-20 years. (see, Bridgwater, A. V., Appl. Catalysis A 116 (1994) 5-47. D. Mohan, et al., Energy and Fuels (2006) 20, 848-889

Starting with the very early work on combustion and gasification processes, it was recognized that inorganic compounds present or added to the biomass strongly affect the behavior of the biomass during the thermal decomposition processes (pyrolysis, combustion, and gasification). However, the objectives of these three processes are different, specifically, pyrolysis processes aim towards maximum yields of organic liquids, with minimum yields of char, and light gases, including $CO/CO_2$ and water. To the contrary, combustion and gasification processes aim towards complete conversion of the biomass carbon to combustible gases.

Further, there are examples of processes wherein a pyrolysis process is combined with a combustion process, such that char formed by the pyrolysis is subsequently combusted or gasified.

In all three thermal processes, the presence of inorganic matter plays a major role in determining yields, kind of products, and product properties. Further, the presence of metals in the biomass plays also a major role in the thermochemical behavior during combustion, gasification and pyrolysis.

In general, depending on the source of the biomass, its history of growth, location, etc. about 20 inorganic species have been found to be present in different kinds of biomass, with the most abundant being Na, K, Ca, Mg, S, Si, Fe, Mn, Al, and P. In some biomass sources, the total concentration of inorganic species can reach 25% based on dry weight of the biomass.

Relating to pyrolysis processes are the flaming and smoldering combustion processes, wherein the flaming combustion involves the gas phase oxidation of the pyrolysis products, and smoldering combustion involves the combustion of residues remaining after evaporation of the volatile components.

The kind of pathways, rates of conversion and yields are strongly affected by the heating conditions and the presence of inorganic matter.

Pyrolysis of cellulose involves two alternative pathways, one at lower temperature involving the decomposition of the glycosyl units to char, $H_2O$, $CO$, $CO_2$; and another at higher temperatures involving the depolymerization of the glycosyl units to volatile oily (tarry) products.

The addition of flame-retardants to cellulosic materials promotes reactions that produce $CO$, $CO_2$, $H_2O$ and char, while reducing the amount of volatile organic tarry products.

Early work on the kinetics and mechanisms of these reactions using cellulosic materials and inorganic additives as flame retardants was based on measurements obtained by Thermo-gravimetric analysis (TGA). (see, F. Shafizadeh, J. Appl. Pyrolysis 6 (1984) 217-232. M. J. Antal, Ind. Eng. Chem. Res. (1995) 34, 703-717. In general, the kinetics, mechanisms, yields and types of products of the pyrolytic processes depend strongly on the composition of the biomass, pretreatments, heating conditions and atmosphere, wherein the process is conducted and catalyst present.

In their original pioneer work, Shafizadeh (see, Cellulose Chemistry and Its Application, T. P. Nevell and S. H. Zeronian (Eds), Chapter 11, "Thermal degradation of cellulose", Ellis Horwood Ltd (198?) p 266) and co-workers used Thermo-gravimetric analysis (TGA); thermal evolution analysis (TEA); evolved gas analysis (EGA); and differential thermal analyses (DTA) to determine the kinetics and mechanisms of the, thermal and thermo-catalytic conversions of cellulosic biomaterials. They showed that the main biomass components (cellulose, hemicellulose and lignin) undergo chemical/physical changes at different temperatures and at different rates. Furthermore, they showed that the addition of inorganic components, in general, lower the temperature of the thermo-catalytic conversion as determined by the DTA, and EGA analyses.

Additionally, the presence of inorganic compounds, whether indigenous or added, selectively promotes the formation of char at the expense of tarry oils.

There is a considerable amount of research work published on the kinetics of biomass decomposition in pyrolysis processes for the production of organic liquids. (see, Antal, M., In Adv. in Solar Energy Vol. 2, Amer. Solar Energy Soc., NY, 1983

A simplified model proposed originally by Shafizadeh (see, F. Shafizadeh and W. F. DeGroot, "Combustion Characteristics of Cellulosic Fuels" in Thermal Uses and Properties of Carbohydrates and Lignins, Academic Press (1976)) describes the decomposition of biomass taking place first through primary reactions producing gas, tar (oil) and char, and subsequently the tar (oil) via undergoes secondary reactions producing gas and char. These reactions take place in parallel, thus complicating the kinetic model for biomass thermal degradation.

Work reported later on (see, Linden, et al., Chem. Eng. Comm. 1988, 65, 207-221) showed that, if a high concentration of inorganic compounds (salts) is present during pyrolysis, the conversion route follows a mechanism enhancing ring fragmentation, thereby yielding higher amounts of lower molecular weight compounds, for example, hydroxyacetaldehyde. When low concentrations of inorganic salts are present on the biomass during pyrolysis, the mechanism of degradation involves a depolymerization producing high molecular weight compounds, such as levoglucosan and fructose. Accordingly, the maximum degradation temperature depends on the amount of metals present on the biomass.

Feldmann, et al. (see, Amer. Chem. Soc., Symp. Ser. No. 144, ACS, Washington, D.C., 1982) showed that adding ash or calcium oxide to lignocellulosic wood biomass prior to pyrolysis of the mixture increases the yield of volatile organic liquids. Both the wood-ash and calcium oxide decreased the yield of the char and increased the yield of the organic liquids.

The work of Hsisheng Teng and Yun-Chow Wei (see, Ind. Eng. Chem. Res. 1998, 37, 3806-3811) is of particular interest. These authors used rice hull biomass in their pyrolysis studies. Using a high resolution DTG analysis technique, they were able to dissect the evolution of volatile materials into three individual components, that is, the lowest temperature (about 350° K) corresponding to the decomposition involving moisture volatilization, next at higher temperatures were the decompositions of the hemicelluloses and cellulose and finally at the highest temperature was the decomposition due to lignin. Another interesting finding of Hsisheng was an observed increase in the organic volatile yields, and a decrease of the char yield, when the rice-hulls were washed with water before pyrolysis. At the same time, the maxima of the decomposition peaks occurred at higher temperatures. The increase in the temperature where the peaks occurred, as well as the increase in the activation energies of the volatilization, was attributed to the washing process, which removed indigenous inorganic salts that are known to decrease the decomposition peak temperatures when present in the biomass and act as catalysts in the thermo-degradation process of the biomass. Further, it was observed that the yield of the volatile organics was increased, while the yield of the residue char was decreased. The cause for these changes was due to removal of soluble organic matter by the washing, which during pyrolysis reacts with other components to form chars.

Gray, R., et al., (see, Ind. Eng. Chem. Process Dev., Vol. 24, No. 3 (1985) 646-65) in their work they used a wood-derived material which was pyrolized in a fluidized bed reactor operated in a nitrogen atmosphere at different temperatures. They acid treated the samples, as well as ion exchanged them with a calcium salt. They measured the yield of gases, aqueous and tar (oily) products, at three different pyrolysis temperatures. Both the acid-treated and calcium exchange samples gave higher tar yields (organic, volatile compounds) than the untreated samples, which gave increased yields of water, char, and gases.

Zaror, C. A. et al., (see, Fuel, (1985), Vol. 64, 990-994) studied the char formation in the catalytic pyrolysis of biomass using different kinds of wood, as such, and impregnated with alkaline salts, which were pyrolized in a Thermo-gravimetric balance and also in a Gray-King Retort. Their data show that the salt-impregnation caused the temperature at which the peak of the maximum mass loss is located to decrease, and all the weight loss curves were shifted to lower temperatures. This confirmed previous work indicating the decrease of the decomposition temperature that was caused by contacting biomass with inorganic salts, while at the same time enhancing devolatilization and increasing the weight loss at lower temperature. Further, they observed that these effects are more pronounced when the biomass is impregnated with sodium and potassium carbonates. Most interesting are their data showing that when the carbonates (K and Na) impregnated feed samples (after impregnation) were washed with water before being subjected to the pyrolysis, they produced much less char and gases and at lower decomposition peak-temperatures.

Varhegyi, G., et al., (see, Energy & Fuels (1988) 8, 267-272) have studied the pyrolytic devolatilization of cellulose and sugar cane bagasse. The samples were impregnated with $MgCl_2$, NaCl, $FeSO_4$, $ZnCl_2$ catalysts. The authors used a sophisticated experimental equipment arrangement by combining the Thermo-gravimetric and Mass Spectrometric instruments, and operating in a continuous simultaneous mode. In general, their data show substantial changes in yields and product distribution, as well as lowering the temperature of the weight-maximum loss peaks.

DeGroot, W., and Shafizadeh, F. (see, Fuel (1988), Vol. 67, 345-361) reported on the thermal decomposition of different kinds of wood and the effects of metal salts (K and Ca) additives. In these studies, the pyrolysis of wood was conducted in a Thermo-gravimetric apparatus (DTG). The wood samples were treated with acid, ion-exchanged with K or Ca salts or impregnated with these salts. One of their observations indicated that the lower temperature decomposition peak, which is assigned to the decomposition of hemicellulose, shifted to a lower temperature, indicating that the presence of indigenous (exchangeable) metals, or additive metals are interacting with the acidic groups of the hemicellulose, thus resulting in decreasing the thermal stability of the hemicellulose component of the wood biomass. Further they observed that the addition of potassium increases the char yield, while it reduces the decomposition (devolatilization) temperature. By contrast, the addition of calcium reduces slightly the char yield, while increasing the decomposition temperature.

In these studies the specific tar yields, and gases, were not measured, but only the complete char residues. However, it is expected that in general, thermal biomass degradations in a pyrolytic process that result in lower char yields, usually such lower char yields are associated with higher tar (organic liquids) yields.

Additionally, it was observed that the results obtained in the pyrolysis depended on the specific mode of application of the particular salt to the biomass chars. For example, potassium carbonate impregnated into the biomass increased its decomposition temperature, while to the contrary, when same salt is ion-exchanged it produces the opposite result.

Related studies were reported by DeGroot, W., and Richards, G. Wei-Pink Pan and G. Richards (see, J. F. Analytical & Applied Pyrolysis (1989) 16, 117-126) where they conducted similar investigations involving the ion exchanging of metal ions on wood and measuring their effect on decomposition temperatures and yields of volatile products. Their technique of measuring these effects involved a combination of DTA and gas-phase FTIR spectroscopy. The ion exchange was done using calcium and potassium acetate salts. Further, the indigenous metals from the wood were removed by acid treatments, resulting in reducing the yields of the volatile products. Potassium ions exchanged into the wood increased substantially the yield of carbon dioxide, while at the same time lowering the temperature of the decomposition peak. It was concluded that at least part of this excessive amount of carbon dioxide is derived from the thermal decomposition of cellulose.

In general, the samples which were acid treated first and subsequently calcium or potassium exchanged gave similar results to those obtained with the untreated materials. These results indicate the important role that the indigenous metals present in the wood play in determining the yields, products and decomposition temperatures of the wood during pyrolysis.

Raveendrank, et al, (see, Fuel (1995), Vol. 74, No. 12, 1814-1816) conducted extensive work on the influence of mineral matter on the pyrolysis of different wood biomass. The experimental apparatus consisted of a dynamic TGA, and a pyrolysis unit. Wood samples included high lignin and low lignin biomass materials. Samples were pretreated, (a) by acid-treatment to remove the natural minerals (indigenous) present in the wood, (b) the acid-treated samples, subsequently impregnated with metals, and (c) synthetic biomass samples prepared by mixing lignin, hemicellulose and cellulose in proportions similar to the compositions found in the natural biomass samples. In these experiments, the yields of gas, char volatiles and temperature of maximum decomposition were measured. The salts used for the impregnation included $Na_2CO_3$, $K_2CO_3$, $ZnCO_3$, NaCl, KCl, $ZnCl_2$, HCl, and NaOH, and were used to treat 13 natural biomass materials plus several synthetic samples.

It was observed that all types of biomass, except three (which contained large amounts of lignin and K), after having been demineralized (by HCl treatment), when pyrolyzed, produced less char and gas and more volatiles. In all cases (except for biomass, from milled husk), the temperature of maximum devolatilization (peak) was increased by the removal of indigenous inorganic matter from biomass.

The authors attributed the exceptional behavior of coir pith, ground nut shell and rice husk due to their high contents of lignin and potassium. Potassium is well known for its catalytic activity in char gasification, yielding large quantities of $CO_2$. Further, it was suggested that changes observed with the use of salt impregnations with different metal salts are due to the nature of the particular cation (i.e., Na, K, Zn, Ca, and Mg) and not due to the anion.

Fahmi, R., et al., (see, R. Fahmi et al, Fuel, 86 (2007) 1560-1569) reported on the effect of alkali metals present or added to two kinds of grasses and two kinds of wood on their catalytic pyrolysis. They used TGA and pyrolysis-GCMS apparatus to measure the thermo-catalytic decomposition, product yields and kinds of products. Acid treatments (HCl) were used to remove the indigenous metals from the samples, which were milled to below 500 µm particle size. High resolution DTG measurements showed the individual peaks for the decomposition of hemicellulose (about 500° K) and the higher temperature (598° K) corresponded to the cellulose component decomposition, which is more thermally stable as it is crystalline, whereas the hemicellulose (semi-crystalline) is less thermally stable. Further, using this high resolution DTG analysis, the intensity of the individual peaks provided relative quantitative estimates of the concentration of the individual components in the biomass samples. For example, the acid pretreatment of Festuca grass resulted in a 900% increase in the yield of levoglucosan during pyrolysis.

Further, a good linear correlation was established in this work between the decrease of the temperature of maximum cellulose degradation (Tmax peak) with increasing metal content (K+Na), present in the char/ash.

Similarly, a good correlation was established showing the increase in the char production with increasing metal content during pyrolysis for the acid-treated and untreated samples. It was concluded that the acid treatment that removed at least most of the metals resulted in decreasing the amount of char formed and increased the yield of organic liquids as well as improving its quality for use as a fuel. Other catalytic biomass pyrolysis studies, using different kinds of catalysts are described in publications 26, 27 and 28. (see, Lappas, A., et al., Fuel 81 (2002, 2087-2095); Samolada, M. C., and Vasalos, I. A., Fuel 70 (1991) 883-890; and Samolada, M. C., et al, Energy and Fuels, 14, (2000), 1161-1167)

U.S. Pat. No. 3,926,947 describes a process in which cellulosic waste materials such as paper and newsprint are treated with an acidic fire retardant that enhances the yield of certain bio-oils during pyrolysis. The fire retardants claimed were: phosphoric acid, ammonium phosphates, ammonium sulphate, and zinc sulphate, which were impregnated into the biomass before subjected to pyrolysis.

U.S. Pat. No. 5,807,952 teaches a process for converting lignins to phenolic compounds by pyrolyzing the lignin in the presence of a strong base like KOH. The lignin and potassium hydroxide powders were mixed and placed into a single stage quench reactor heated to 600° C. Vapors were analyzed with a mass spectrometer.

U.S. Pat. No. 5,395,455 describes a process for producing anhydrosugars from lignin and cellulose containing biomass by pyrolysis, using a strong acid pretreatment of the biomass before pyrolysis.

Besides claiming the acid-removal of the natural minerals from the biomass, it also claims that certain anions, such as sulphate, sulphite or nitrate can be added to the acid-treated biomass by impregnation. Further, after the strong acid-treatment (digestion) of the biomass, soluble organic material can be separated and the residue then pyrolyzed.

The disclosures of WO 2007/128799 A1 are incorporated herein by reference. This patent application discloses methods of embedding particulate inorganic matter into biomass particles. To allow the formation of said particles into the bulk of the biomass particles, swelling of the wood was used to enlarge/create openings large enough to accommodate the in situ formation of particulate inorganic matter in the biomass.

DETAILED DESCRIPTION OF THE INVENTION

Biomass derived from forestry, agriculture and cellulosic waste materials, due to its compact strong physical construction and its chemical nature containing primarily cellulose, hemicellulose, lignin, mineral matter and other materials, resists conversion processes such as thermal, hydrothermal, and enzymatic processes, which are used to convert said biomass to fuels and chemicals.

The most abundant and useful components for the conversion, the cellulose and hemicellulose, are bundled up and sealed by the protective coating provided by the lignin component. Therefore, a direct exposure of the cellulose and hemicellulose to chemical reagents or even to thermal conditions is prevented by the lignin and other foreign, noncellulosic substances present.

Additionally, any primary product resulting from the contact of the biomass with a chemical reagent or during thermo-decomposition, and derived from one or more of the components in the biomass substance, is diffusionally restricted from escaping the reaction zone due to the lack of bulk accessibility in the biomass particle.

The reaction products and intermediates being restricted in the bulk of the biomass, and remaining in contact within themselves for longer periods, can further interact within themselves, or can interact with unreacted segments of the biomass or with other components present, to form secondary products. These secondary products are not only undesirable, but their presence in the biomass substrate can alter the reaction pathway, thereby causing changes in the yields and kinds of products obtained from the commercial process.

Further, the three major biomass components (cellulose, hemicelluloses and lignin) have different reactivities towards acids and bases, as well as having different thermal stabilities, and decompose at different rates to different products like organic volatiles, chars, water and gases, including $CO/CO_2$. Unfortunately, the production of chars and gases are produced at the expense of the yield of organic volatiles, thus making the known commercial conversion processes inefficient and costly.

Therefore, there is a need for an improved pretreatment process that will modify the biomass-feed in such a way that when subjected to thermo-conversion (pyrolysis) processes, it will yield more volatile condensable oily products and less char, $CO/CO_2$, other gases and water.

Additionally, such modification of the biomass-feed must render the feed more easily digested by enzymes to produce high yields of sugars in the enzymatic conversion to ethanol, while using lesser amounts of enzymes.

It has been discovered that by enhancing the natural tendency of lignocellulosic biomass to swell with water under thermal and mechanical treatments, the internal compacted bulk of the biomass particle is disrupted, thus creating voids, openings, surface area and accessibility to the exterior of the particle. Additionally, the swelling properties of the biomass are further enhanced by utilizing the acidic property of the biomass that causes it to react as a monobasic acid by neutralizing it with a strong base. Thus this modified biomass, when subjected to thermal or enzymatic conversions, yields more of the desirable products, such as oils or ethanol.

Additionally, by optimizing the swelling conditions under thermal and mechanical treatment, the water in the swollen biomass acts as a kind of "chimie-douce" treatment, which results in dissolving and hydrolyzing, and cleaning up foreign materials in the bulk of the biomass, such as soluble salts and resins, etc. The removal of these undesirable materials can be accomplished by extruding the swollen biomass wherein the swollen biomass is squeezed through the small orifices under pressure, thus de-sorbing the water containing the soluble extracted materials.

The removal of the water soluble extractables "unblocks" the openings between the cells. This allows penetration of the water molecules below the external surface of the biomass particle.

Further, the "cleansing" effectiveness of the "chimie-douce" process can be further increased by using an acidic solution or a basic solution to enhance the swelling. The removal of the water from the swollen biomass containing the extractables, can be conducted in a high pressure filter press.

The removal of the extractables is an important process as it causes, under thermoconversion, higher yields of char.

Another embodiment of this invention involves, as a first step, the swelling of the biomass by water, with an optional dewatering step to remove the extractables, followed by an addition of soluble salt solution, acid or a base. Yet another embodiment comprises the steps of (i) swelling the biomass material with a solvent, optionally aided by pH control, application of mechanical action, the incorporation of additive(s) and temperature control; (ii) removing solvent from the swollen biomass material by applying mechanical action to the biomass material, and (iii) adding an inorganic catalytic material. In a further embodiment, the inorganic catalytic material is dissolved in a solvent, such as an aqueous liquid. In still a further embodiment the catalytic material is in particulate form. Additionally, the catalytic material can comprise an inorganic salt preferably with a cation selected from the group consisting of K, $NH_4$, Na, Ba, Mn, Mg, Ca, Li, Zn, and mixtures thereof and with an anion selected from the group consisting of OH, $CO_3$, $SO_4$, $PO_4$, Cl, $NO_3$ and mixtures thereof. In yet another embodiment of the invention, step (iii) comprises mechanical action and results in a particle size reduction of the biomass material.

The addition of soluble salts or colloidal suspensions to the swollen biomass provides another process wherein "additives" can be incorporated into the bulk of the biomass particles. The additional porosity created by the water swelling (not accessible in the raw [untreated] biomass) provides a "hosting" volume for the accommodation of additive materials, such as catalysts in the interior bulk of the biomass particle. Accordingly, the catalytic material may comprise and insoluble inorganic material, in a colloidal or nanoparticular form. The insoluble inorganic material is selected from the group of refractory oxides, zeolites, cationic clays, anionic clays, layered hydroxide materials, hydrotalcites, and mixtures thereof.

Accordingly, the catalytically active sites (i.e., metal ions) are now located close to the individual components present in the biomass (i.e., lignin, hemicellulose and cellulose) and interact directly with the reactive sites of these components at the initiation of the thermoconversion process. In an embodiment of the invention, the product of the process described herein is used in a enzymatic hydrolysis process, a thermoconversion process. Thermoconversion process may be selected from the group consisting of pyrolysis, catalytic cracking, gasification, steam gasification, hydrotreatment, and combinations thereof. The thermoconversion process may be carried out in a fixed bed reactor, a fluidized bed reactor, fluidized catalytic reactor (FCC), or an ebbulated bed reactor.

Further, the inorganic salts implanted into the bulk of the biomass particles, not only act as near next-neighbor catalyst sites, but also act as a heat-sink, thus increasing the heat transfer rate into the interior of the biomass particle.

This process is distinctly different from the known prior-art processes, wherein the catalytic metals are deposited on the exterior surface of the biomass particle, such as, for example, using impregnation techniques, or by physical mixing or by dusting on the biomass fine powders of such catalyst). In these cases, the devolatilized oily vapors generated in the bulk, need to travel throughout the biomass interior volume, and only when they exit the particle, see (interact) with the catalyst particle, which is located on the external surface of the biomass particle.

The devolatilized oily vapors, while traveling throughout the bulk of the particle, not only react with other reactive regions of the three main components (lignin, hemicellulose and cellulose), but also react with themselves, as the residence time within the particle is increased under (internal) pressure and high temperature.

Therefore, the devolatilized condensable oily vapors, in the case of having the catalyst sitting on the exterior surface of the biomass particle, after having undergone interactions among themselves and interactions with other regions of the biomass, then react with the catalyst, which sits on the surface. In the case of the process of this invention, the devolatilized oily vapors not only have increased accessible volume to escape away fast from the biomass residue char, but they are able to interact with the catalyst located in the close proximity within the bulk volume, at their first on-set formation.

Metal compounds deposited on the exterior surface of the particles by means of chemical and/or mechanical means, when subjected to a thermo-conversion like pyrolysis, as the surface of the particle is first heated this inorganic matter interacts first with the initial vapors produced in the outer skin area of the biomass and form chars containing mostly metal oxides, which are covering the outer surface of the biomass particle. Said skin-chars, containing most of the inorganic matter, covering the external surface of the biomass particle, acts further to alter the mechanisms of the remaining thermo-devolatilization process and to increase the yields of gases and char at the expense of volatile oily condensable vapors.

An effective severe swelling of the biomass causes disruption of the internal bulk hydrogen bonding links between components and in general it upsets the compact nature of the bulk biomass particle.

However, an even more disruptive effect is caused when the sorbed water phase in the bulk of the biomass particle, is suddenly heated up to vaporize within the bulk biomass particle. This creates an "in-situ" high pressure steaming or "in-situ" steam explosion within the solid biomass particle, which not only can cause further hydrolysis, but also causes additional disruption of the compact interior texture, thus creating more internal open volume and increased accessibility to the exterior of the particle. Suitable fast heating sources are:
microwaves, flash drying, and AC induction heating.

Another embodiment of this invention involves enclosing the water swollen biomass in a closed container, which is heated to temperatures above 100° C. This treatment allows the interior, as well as the exterior of the biomass particles, to be exposed to high pressure steam.

Such treatment increases the destruction of the bonding between components, causes additional hydrolysis and loosening of the compact biomass substrate, thus creating more openness to the interior bulk of the particle, as well as increased accessibility to the exterior.

In a different mode of practicing this invention, the swollen biomass is dried first and then milled. It was observed that the treated biomass was more brittle than the raw biomass, which caused the milling to be more effective in producing smaller particles with a less severe milling.

In another embodiment the biomass is comminuted first prior the treatment according to this invention.

In another mode of operation of this invention, the comminuting and swelling is conducted simultaneously.

Process [00111] and [00112] are conducted in the presence of an additive(s).

Thus, the invention has been described by reference to certain embodiments discussed above. It will be recognized that these embodiments are susceptible to various modifications and alternative forms well known to those of skill in the art. For example, the swelling may be modified by the milling process.

Many modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A process for pretreating a lignocellulosic biomass material for conversion to bio-oil, said process comprising:
   (i) contacting the lignocellulosic biomass material with an aqueous fluid, to form a swollen solid lignocellulosic biomass;
   (ii) dewatering the swollen biomass to form a solid modified lignocellulosic biomass material having an increased bulk porosity; and
   (iii) subjecting the solid modified lignocellulosic biomass material to enzymatic hydrolysis, thermoconversion, or combinations thereof.

2. The process of claim 1 wherein the step of contacting the lignocellulosic biomass with an aqueous fluid is carried out at an elevated temperature in the range of from 35° C. and 100° C.

3. The process of claim 1 wherein the step of contacting the lignocellulosic biomass with an aqueous fluid is carried out at an elevated temperature that is greater than 100° C. and is carried out under autogenous pressure.

4. The process of claim 1 further comprising subjecting the solid modified lignocellulosic biomass material to drying, milling, comminuting or combinations thereof.

5. A pre-treatment process for preparing a lignocellulosic biomass material for conversion to a bio-oil, said pre-treatment process comprising the steps of:
   (i) swelling the biomass material with a solvent, optionally aided by pH control, application of mechanical action, the incorporation of additive(s) and temperature control;
   (ii) removing solvent from the swollen solid biomass material by applying mechanical action to the solid biomass material to form a solid modified lignocellulosic biomass material having an increased bulk porosity; and
   (iii) subjecting the solid modified lignocellulosic biomass material to enzymatic hydrolysis, thermoconversion, or combinations thereof.

6. The pre-treatment process of claim 5 wherein the solvent is an aqueous liquid.

7. The pre-treatment process of claim 5 wherein the mechanical action results in a particle size reduction of the biomass material and is exerted by equipment selected from the group consisting of high shear mixers, kneaders, colloid mills, planetary mixers, mix-mullers, extruders, pressure filters, centrifuges and/or ball mills or other comminuting equipment.

8. The process of claim 5 wherein the ash content of the biomass material is reduced to less than 5 wt %, based on dry weight of the biomass material.

9. The process of claim 5 wherein Fe content of the biomass material is reduced to less than 2,000 mg/kg, based on dry weight of the biomass material.

10. The process of claim 5 wherein the solvent of step (i) comprises an inorganic acid or an inorganic base.

11. The process of claim 5 comprising the additional step of adding an inorganic catalytic material before subjecting the solid modified lignocellulosic biomass material to enzymatic hydrolysis, thermoconversion, or combinations thereof.

12. The process of claim 11 wherein the inorganic catalytic material is dissolved in a solvent.

13. The process of claim 12 wherein the solvent is an aqueous liquid.

14. The process of claim 13 wherein the catalytic material comprises an inorganic salt.

15. The process of claim 14 wherein the catalytic material comprises a cation selected from the group consisting of K, $NH_4$, Na, Ba, Mn, Mg, Ca, Li, Zn, and mixtures thereof.

16. The process of claim 15 wherein the catalytic material further comprises an anion selected from the group consisting of OH, $CO_3$, $SO_4$, $PO_4$, Cl, $NO_3$ and mixtures thereof.

17. The process of claim 14 wherein the catalytic material comprises an insoluble inorganic material, in a colloidal or nanoparticular form.

18. The process of claim 17 wherein the insoluble inorganic material is selected from the group of refractory oxides, zeolites, cationic clays, anionic clays, layered hydroxide materials, hydrotalcites, and mixtures thereof.

19. The process of claim 5 wherein the thermoconversion process is selected from the group consisting of pyrolysis, catalytic cracking, gasification, steam gasification, hydrotreatment, and combinations thereof.

20. The process of claim 19 wherein thermoconversion process is carried out in a fixed bed reactor, a fluidized bed reactor, fluidized catalytic reactor (FCC), or an ebbulated bed reactor.

* * * * *